United States Patent
Timmins et al.

(10) Patent No.: US 12,227,730 B2
(45) Date of Patent: Feb. 18, 2025

(54) SYSTEM AND METHOD FOR ASEPTIC SAMPLING AND FLUID ADDITION

(71) Applicant: GLOBAL LIFE SCIENCES SOLUTIONS USA LLC, Marlborough, MA (US)

(72) Inventors: Mark Robert Timmins, Chelmsford, MA (US); Matthew Sherman, West Newton, MA (US); Yasser S. Ali, Westborough, MA (US); Marc Picardo, Ashland, MA (US); Keith Benoit, Grafton, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 857 days.

(21) Appl. No.: 16/951,280

(22) Filed: Nov. 18, 2020

(65) Prior Publication Data
US 2022/0154127 A1    May 19, 2022

(51) Int. Cl.
*C12M 1/32* (2006.01)
*C12M 1/00* (2006.01)
*C12M 1/26* (2006.01)
*G01N 1/28* (2006.01)

(52) U.S. Cl.
CPC ............ *C12M 33/06* (2013.01); *C12M 27/20* (2013.01); *C12M 29/04* (2013.01); *C12M 33/04* (2013.01); *G01N 1/28* (2013.01)

(58) Field of Classification Search
CPC ...... C12M 33/06; C12M 27/20; C12M 29/04; C12M 33/04; C12M 33/07; G01N 1/28; G01N 2001/1418; G01N 1/14
See application file for complete search history.

(56) References Cited

U.S. PATENT DOCUMENTS

| | | | | |
|---|---|---|---|---|
| 4,937,194 A | * | 6/1990 | Pattillo | C12M 33/07 141/10 |
| 5,837,444 A | * | 11/1998 | Shah | A61K 9/0024 422/534 |
| 9,677,975 B2 | * | 6/2017 | Zhang | C12M 37/02 |
| 9,733,158 B1 | * | 8/2017 | Wiederin | G01N 1/14 |

(Continued)

FOREIGN PATENT DOCUMENTS

| CN | 111235018 | 6/2020 |
|---|---|---|
| EP | 3183334 | 6/2017 |

(Continued)

OTHER PUBLICATIONS

Translation of JP2018088133A, Nakayama Daisuke, May 10, 2012 (Year: 2012).*

(Continued)

*Primary Examiner* — Samuel P Siefke
*Assistant Examiner* — Henry H Nguyen
(74) *Attorney, Agent, or Firm* — Grogan, Tuccillo & Vanderleeden LLP

(57) ABSTRACT

A sampling system includes a graduated sampling chamber configured for fluid connection to a sample source, a pump device configured for fluid connection with the sampling chamber, and a sterile air filter intermediate the pump device and the sampling chamber, wherein the pump device is selectively actuatable to draw a volume of fluid from the sample source into the sampling chamber.

9 Claims, 6 Drawing Sheets

(56) References Cited

U.S. PATENT DOCUMENTS

| | | | |
|---|---|---|---|
| 10,190,950 B2 | 1/2019 | Griffin et al. | |
| 10,465,157 B2 | 11/2019 | Zhang et al. | |
| 2005/0191620 A1* | 9/2005 | McDevitt | C12Q 1/6816 |
| | | | 436/523 |
| 2014/0057344 A1* | 2/2014 | Brauner-Sreuther | |
| | | | B01D 21/0042 |
| | | | 210/512.3 |
| 2014/0080113 A1* | 3/2014 | Mui | A61B 5/15003 |
| | | | 422/44 |
| 2014/0123777 A1* | 5/2014 | Newbold | G01N 1/14 |
| | | | 73/864.63 |
| 2017/0362556 A1 | 12/2017 | Komae et al. | |
| 2018/0251713 A1* | 9/2018 | Angelescu | C12M 1/34 |
| 2019/0351113 A1* | 11/2019 | Min | B01D 63/16 |
| 2021/0332313 A1* | 10/2021 | Damacherla | C12M 27/02 |

FOREIGN PATENT DOCUMENTS

| | | | |
|---|---|---|---|
| JP | 2012088133 A * | 5/2012 | |
| WO | 2016026672 A1 | 2/2016 | |
| WO | 2016066766 A1 | 5/2016 | |
| WO | 2016066768 A1 | 5/2016 | |
| WO | 2016091744 A1 | 6/2016 | |

OTHER PUBLICATIONS

PCT International Search Report dated May 13, 2022 from corresponding International Application No. PCT/EP2021/079802 filed Oct. 27, 2021.

* cited by examiner

SYSTEM AND METHOD FOR ASEPTIC SAMPLING AND FLUID ADDITION

BACKGROUND

Technical Field

Embodiments of the invention relate generally to aseptic sampling and, more particularly, to a system and method for adding or removing, including for sampling, a predetermined volume of fluid or cells to/from a cell culture in a bioreactor in a functionally closed manner.

Discussion of Art

Typically, in a cell culture process, growth media is used to nourish cells and carry away cell-secreted products. The growth media is provided continuously or intermittently to a culture vessel for in vitro culture of biological cells for, for example, recovery of cell-secreted proteins from the culture vessel, and/or other purposes, such as expansion of cells. Further, the growth media is provided to the culture vessel via a flow path that is formed using suitable tubing. Often, this tubing is present as a closed system, where the closed system includes provisions for periodic or continuous replenishment of the growth media by introduction of fresh growth media It is often desirable to monitor the cell culture process. Further, monitoring of the growth media in the cell culture vessel and/or at one or more points in the flow path is an effective way of monitoring and/or controlling the cell culture process. Typically, monitoring of the cell culture process is performed by installing sensors in the culture vessel, as well as periodically drawing a portion of the growth media or a sample having a mix of cells and the culture media from the culture vessel for analysis. Thus, for example, analysis of the growth media before, during, and after passage through the culture vessel for monitoring one or more process conditions, such as nutrient components, cell-secreted proteins, cell-secreted metabolites, or the like may provide significant information regarding one or more of a number of viable cells in the culture vessel, a rate of nutrient consumption by the cells, a rate of product secretion, cell growth rates, stages of cell growth, presence or absence of subdivision of cells, and the like. Such information may be used to monitor the closed system and/or to indicate changes that may require alteration of the process conditions, the composition of the growth media, or the like to optimize the cell culture process.

Further, it is required for the cell culture process to be carried out under aseptic conditions, as in the absence of the aseptic conditions the cells may be contaminated, thereby resulting in contamination of products recovered therefrom and/or loss of cell viability. As a consequence, cell culture systems and their component parts are often initiated and maintained under sterile conditions, with each portion or the entirety of the systems being sterilized prior to commencement of the process, and using sterile culture medium and uncontaminated seed cell stocks.

However, during sampling there is a need to ensure that sampling of the culture media or the sample is carried out in a manner to prevent introduction of contaminants into the pre-established sterile system. Conventional techniques for accomplishing this sterile withdrawal of the sample are elaborate, expensive, and time consuming. In addition, the conventional techniques for sterile withdrawal of the sample may compromise sterility of the culture vessel. By way of example, in some of the existing systems, the area from which the sample is to be drawn, be it the culture vessel or the flow path to or from the culture vessel, is provided with a sample port such as in the form of a short segment of tubing or other appropriate structures. The system is then accessed via this sample port to withdraw a desirable quantity of the sample. Further, a portion of a biological inoculum, which is a mixture of the cells and the growth medium, is drawn from the culture vessel at different instances in time to monitor the cell culture process that is taking place in the culture vessel.

Each sampling instance requires drawing a portion of the sample from the culture vessel. Various tubes are attached to the ports or are passed through the ports of the culture vessel at different instances in time for different sampling instances. Any leakage or contamination in the tubing or in the connection between the culture vessel and the tubing may introduce contaminants in the culture vessel. Additionally, every sampling instance is accompanied by a user attaching some sort of tubing or device either directly or indirectly to the culture vessel, thereby increasing the risk of contamination of the inoculum. By way of example, a plastic sampling bag or a syringe may be attached to the tubing to collect the sample that is drawn from the culture vessel. In addition to the increased risk of introduction of the contaminants due to coupling of the sampling bags/syringes to the culture vessel, there is also a likelihood of a portion of the sample being left in the tubing after the sampling instance. This residual sample may then be inadvertently carried over to the next sampling instance, thereby jeopardizing the purity of the sample obtained in the next sampling instance. Further, each sampling instance increases the likelihood of contamination of the inoculum.

The challenge, therefore, is making repeat removals (e.g., sampling for offline QC) from a single-use bioreactor or other vessel in a functionally closed manner, so as to minimize the risk of contaminating the culture. Another current sampling process involves a single-use syringe connected to a swabable Luer port on the bioreactor vessel. Neither the port nor the Luer, however, are considered closed—the Luer because it is exposed to the atmosphere (necessitating swabbing it with alcohol before and after use to prophylactically attempt to prevent contamination) and the syringe for the same reason, plus the risk that the plunger could accidentally be fully removed from the barrel. Moreover, the use of this approach brings with it the risk of being able to push fluid back into the vessel, which further increases the risk of contamination.

More recent efforts to address these limitations have used a stop-cocked manifold to reduce the risk of contamination, using stopcocks to (manually) manage flow, and commercial vacutainers to ensure that flow is outward only, not inward back toward the vessel. However, such stopcocks must still be connected via an open step. A limitation of this design concept is that the volume to be collected cannot be precisely controlled (i.e., the volume pulled from the vessel must be some increment of the available vacutainer tube volumes, the smallest of which is 2 mL).

In view of the above, there is a need for a system and method for adding or removing a known volume of fluid to or from a fluidic vessel in a functionally closed manner.

BRIEF DESCRIPTION

In an embodiment, a sampling system is provided. The sampling system includes a graduated sampling chamber configured for fluid connection to a sample source, a pump device configured for fluid connection with the sampling chamber, and a sterile air filter intermediate the pump device and the sampling chamber, wherein the pump device is selectively actuatable to draw a volume of fluid from the sample source into the sampling chamber without the volume of fluid contacting the pump device.

In another embodiment of the invention, a method for sampling is provided. The method includes the steps of connecting a sampling chamber to a sample source, and actuating a pump to draw a volume of fluid from the sample source through a valve, and into the sampling chamber without the volume of fluid contacting the pump, wherein the valve is configured to prevent backflow of fluid from the sampling chamber to the sample source.

In yet another embodiment, a bioprocessing system is provided. The bioprocessing system includes a cell culture vessel, and a first assembly for adding a first fluid to the cell culture vessel. The first assembly includes a first chamber configured for fluid connection to a source of the first fluid via an inlet port in the first chamber, and for fluid connection to the cell culture vessel via an outlet port in the first chamber, a first pump device configured for fluid connection with the first chamber, a first valve intermediate the first chamber and the source, the first valve permitting unidirectional flow from the source to the first chamber, and a second valve intermediate the first chamber and the cell culture vessel, the second valve permitting unidirectional flow from the first chamber to the cell culture vessel. The first pump device is selectively actuatable to draw a volume of the first fluid from the source into the first chamber, and to push the volume of fluid from the first chamber into the cell culture vessel. The bioprocessing system also includes second assembly for removing a second fluid from the cell culture vessel. The second assembly includes a second chamber configured for fluid connection to the cell culture vessel via an inlet port in the second chamber, and for fluid connection to a collection vessel via an outlet port in the second chamber, a second pump device configured for fluid connection with the second chamber, a third valve intermediate the cell culture vessel and the second chamber, the third valve permitting unidirectional flow from the cell culture vessel to the second chamber, and a fourth valve intermediate the second chamber and the collection vessel, the fourth valve permitting unidirectional flow from the second chamber to the collection vessel. The second pump device is selectively actuatable to draw a volume of the second fluid from the cell culture vessel into the second chamber, and to push the volume of fluid from the second chamber into the collection vessel.

DRAWINGS

The present invention will be better understood from reading the following description of non-limiting embodiments, with reference to the attached drawings, wherein below:

DETAILED DESCRIPTION

Figure 1:
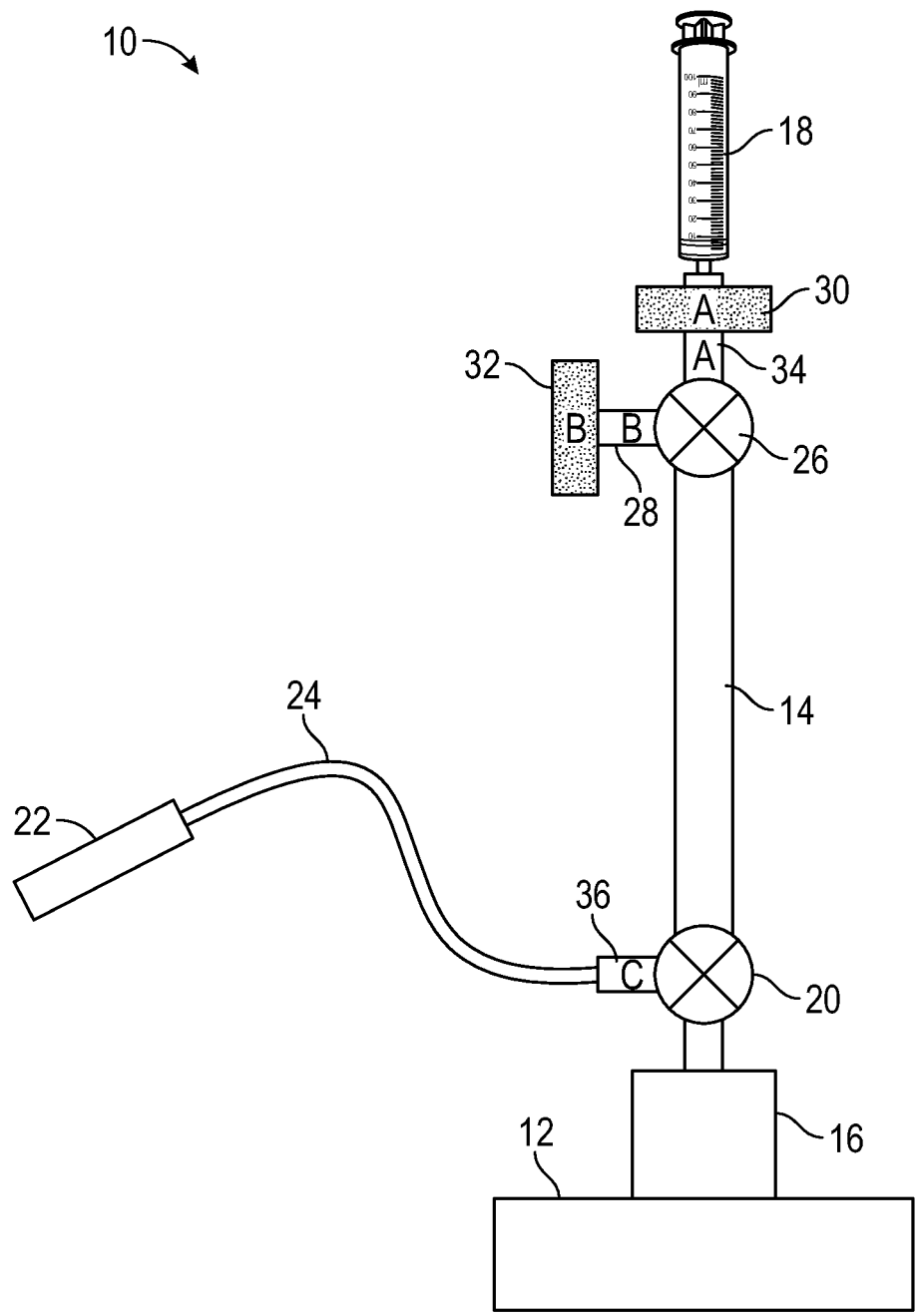
FIG. 1 is a schematic representation of an exemplary sampling assembly configured to aseptically draw one or more samples from a sample source, according to an embodiment of the invention.

Reference will be made below in detail to exemplary embodiments of the invention, examples of which are illustrated in the accompanying drawings. Wherever possible, the same reference characters used throughout the drawings refer to the same or like parts.

Embodiments of the invention relate to pump devices and related methods to add or remove a known volume of fluid to or from a fluidic vessel in a functionally closed manner. In particular, embodiments of the invention center around a graduated chamber, stopcocks, check valves, sterile filters, and sterile-weldable tubing, but is generalizable to other similar or equivalent embodiments. In its simplest form the pump device may be manually operated, but the operation could be automated without fundamentally altering the embodiments of the invention.

The embodiments of the invention disclosed herein, therefore, address the challenge of the prior art by utilizing sterile-weldable tubing to make the connections (though this aspect is generalizable to other means of aseptic connections, such as self-wiping connectors), and then using a syringe outboard of a sterile filter as a pump to draw fluid from a bioreactor or culture vessel, and then push it to the sample collection vessel or receptacle. Alternately, in an embodiment, the graduated chamber could itself be used as the collection vessel. The invention described herein allows for either stopcocks (which must be actuated, either manually or mechatronically), or check valves (which require no intervention) to ensure fluid flow in only one direction.

As disclosed hereinafter, the simplest embodiment includes a graduated chamber into which the fluid is first collected (graduated so that the user may visually gauge and control how much sample is pulled), and from which the fluid is discharged to a collection vessel. It is envisioned that the syringe action could be automated, and the sample volume metered that way (rather than by eyeball) without departing from the broader aspects of the invention.

This concept can be applied both to push fluid into a closed vessel as well as to remove it from said vessel. The only difference in practice would be the direction of the check valves. In one embodiment, in which the closed vessel is a cell culture chamber, a pair of such devices (of appropriate volumetric capacity) could be used to manually, semi-manually, or automatically effect perfusion (i.e., balanced simultaneous and continual addition of fresh media and removal of spent media) into and out of said vessel.

As used herein the phrase, "biological samples" refers to any particle(s), substance(s), extract(s), mixture(s), and/or assembly(ies) derived from or corresponding to one or more organisms, cells, and/or viruses. As will be appreciated, cells which may be cultured in an automated cell management system includes one or more cell types including, but not limited to, animal cells, insect cells, mammalian cells, human cells, transgenic cells, genetically engineered cells, transformed cells, cell lines, plant cells, anchorage-dependent cells, anchorage-independent cells, and other cells capable of being cultured in vitro. The biological sample also includes additional components to facilitate analysis, such as fluid (for example, water), buffer, culture nutrients, salt, other reagents, dyes, and the like. Accordingly, the biological sample may include one or more cells disposed in a growth medium and/or another suitable fluid medium.

As used herein, the term "sterile" or "sterile environment" refers to an environment that is substantially free of unintended microorganisms.

Moreover, as used herein, the term "sample source" refers to any suitable apparatus, such as a large fermentation chamber, bioreactor, bioreactor vessel and/or culture vessel, for growing organisms such as bacteria or yeast under controlled conditions for production of substances such as pharmaceuticals, antibodies, or vaccines, or for the bioconversion of organic waste. Further, the term "sample source" includes vessels for both aerobic and anaerobic cultivation of microbial, animal, insect and plant cells, and thus encompassing a fermentor.

Further, as used herein, "cell culture" entails growth, maintenance, differentiation, transfection, or propagation of cells, tissues, or their products.

Also, as used herein, the term "biological inoculum" refers to cell culture, cells suspended in growth media, suspension cells, cell aggregates, cells attached to beads and suspended in the growth media, and the like. Further, the term "biological inoculum" also refers to various cell types, such as, but not limited to, mammalian cell types (for example, Chinese Hamster Ovary (CHO), human embryonic kidney (HEK), human embryonic stem cells (hESC), primary human cells, T-cells, and the like), insect cell types, plant cell types, microbial cell types, and the like.

Moreover, as used herein, the phrase "growth medium" or "growth media" is used to refer to a liquid solution used to provide nutrients (for example, vitamins, amino acids, essential nutrients, salts, and the like) and properties (for example, similarity, buffering) to maintain living cells (or living cells in a tissue) and support their growth. Commercially available tissue growth medium is known to those skilled in the art. The phrase, "cell growth medium" as used herein means tissue growth medium that has been incubated with cultured cells in forming a cell culture; and more preferably refers to tissue growth medium that further includes substances secreted, excreted or released by cultured cells, or other compositional and/or physical changes that occur in the medium resulting from culturing the cells in the presence of the tissue growth medium.

Additionally, as used herein, the term "sampling instance" may be used to refer to an event of drawing a sample from a sample source at a given instance in time.

Further, as used herein, the term "aseptic sampling" refers to sampling while preventing entry of contamination or external impurities in the sample source or associated components.

Also, as used herein, the term "tubing" may refer to at least a portion of one or more of a sampling conduit, a recovery conduit, and one or more sub-conduits.

As used herein, the term "fluid communication" refers to a relationship between two components by which fluid can be permitted to flow from one component to the other.

FIG. 1 illustrates a sampling assembly 10 (also referred to herein as sampling system 10) configured for aseptic sampling of one or more samples from a sample source 12. In certain embodiments, the sample source 12 may be a suitable culture vessel that is configured for cell culture, such as, but not limited to, cell expansion and growth. Further, the sample source 12 may be configured to house a biological inoculum. In some embodiments, aseptic sampling may be performed to monitor the cell culture process occurring in the sample source 12. A sampling performed at a given time may be referred to as a sampling instance. In one embodiment, a plurality of sampling instances may be performed using the sampling assembly 10 in a time efficient and aseptic fashion.

As shown in FIG. 1, the sampling assembly 10 (also referred to herein as sampling system 10) includes a graduated sampling chamber 14 configured for fluid connection to the sample source 12, such as via connection to a port 16 on the sample source 12, and a pump device such as a syringe 18 configured for fluid connection to the sampling chamber 14. The size of the sampling chamber 14 may be selected according to the particular application or sampling operation carried out, and may range from about 0-5 mL, or from about 1-3 mL, although smaller or larger collection volumes are also envisioned by utilizing an appropriately sized chamber. In particular, it is contemplated that to carry out certain processes, the volume of the sampling chamber 14 may be tens or hundreds of milliliters. The graduated chamber 14, by its definition, has a plurality of graduations or markings enabling a user to see the amount of fluid contained within the sampling chamber 14. In an embodiment, the sampling assembly 10 includes a first three way valve 20 intermediate the graduated sampling chamber 14 and the sample source 12, such that the graduated sampling chamber 14 can be selectively placed in fluid communication with the sample source 12 and/or a receptacle 22 connected to the valve 20 via tubing 24, as discussed in detail hereinafter. In an embodiment, the receptacle 22 is a vacutainer collection tube, and the tubing 24 is a length of weldable PVC or similar material. The sampling assembly 10 additionally includes a second three way valve 26 intermediate the graduated sampling chamber 14 and the syringe 18, such that the graduated chamber 14 can be selectively placed in fluid communication with the syringe 18 and/or with another device through secondary port 28 of the three way valve 26.

While FIG. 1 illustrates the use of a syringe 16, other manual, semi-automatic, or automatic pump devices (e.g., a motorized pump) may also be utilized without departing from the broader aspects of the invention. In an embodiment, the valves 20, 26 may be pinch valves or stopcocks, although other types of valves known in the art configured to provide for multiple flowpaths between components may also be utilized. It is contemplated that the valves 20, 26 can be manually controlled or controlled automatically via an actuator.

With further reference to FIG. 1, the sampling assembly 10 also includes a sterile air filter 30 positioned in the flowpath between the pinch valve 26 and the syringe 18, as well as a sterile air filter 32 associated with port 28 (e.g., within a flowpath connecting an auxiliary device (not shown) to the pinch valve 26 via port 28).

In use during a sampling operation, the first valve 20 is controlled to a position to place the sample source 12 in fluid communication with the graduated sampling chamber 14, while the second valve 26 is controlled to a position to place the syringe 18 in fluid communication with the sampling chamber (via port 34). The syringe 18 is then utilized to draw or pull a desired volume of fluid from the sample source 12 into the graduated sampling chamber 14. As indicated above, the graduations on the chamber 14 are utilized to easily verify when a desired amount of fluid has been drawn into the chamber 14. Once a desired volume of fluid is present in the chamber 14, the valve 26 is controlled to place the port 28 in fluid communication with the chamber 14, and the valve 20 is actuated to fluidly isolate the sample source 12 from the chamber 14, and to place the receptacle 22 in fluid communication with the chamber 14. In the case where the receptacle 22 is a vacutainer, upon enabling fluid connection between the receptacle 22 and the chamber 14, the vacuum environment within the receptacle 22 pulls the fluid within the chamber 14 into the tubing 24 and receptacle 22, displacing it with air let in through the sterile air filter 32 and port 28 in the valve 26. In such case, it is envisioned that the receptacle 22 is large enough to completely empty the chamber 14 plus the tubing 24. In an embodiment, the tubing 24 may be selected to be long enough so as to conveniently position the receptacle 22 at a location where it can be easily accessed for sampling and analysis.

In addition to verifying by sight using the graduated markings, to determine the amount of fluid drawn into the chamber 14, in other embodiments, the fill volume of the chamber 14 may be ascertained by automated optical sensing methods and/or by weight.

In an embodiment, the receptacle 22 need not be a vacutainer. In such embodiments, a syringe or other pump device fluidly connected to chamber 14 through valve 26 can be utilized to push the volume of fluid present in the chamber 14 to the receptacle 22. In particular, air injected through either port 28, 34, for example by syringe 18, may be utilized to push the volume of fluid all the way to the receptacle 22. In either case, the presence of the sterile air filters 30, 32 ensures that any air entering the system 10 is sterile. Once the sample is collected in the receptacle 22, the receptacle 22 can be sterile-welded off and replaced with another receptacle for further sample collection.

In an embodiment, prior to connecting another sample collection receptacle a purge step may be carried out to clear the chamber 14 and tubing 24, if desired. This purge step may be carried out in a variety of ways. In one embodiment, a waste flush receptacle (not shown) may be connected to the port 36 on the valve 20 via tubing 24 so that the holding chamber 14, valve passages and/or tubing 24 can be flushed before further sample collection. For example, in an embodiment, the sampling assembly 10 may include a reservoir of sterile fluid such as water or saline connected to port 28 (or another port, not shown) that is utilized to flush the chamber 14 and the tubing 24 once the sample has been collected, flushing with air when done, and then connecting a new sample collection receptacle to the tubing 24. A similar purge or flushing process is disclosed below in connection with FIGS. 4 and 5.

In another embodiment, another vacutainer may be connected to tubing 24 so that air can be drawn into the chamber 14 through one of the sterile air filters 30, 32 and passed through the chamber 14 and tubing 24. In yet another embodiment, a syringe of saline or other fluid may be connected to one of the ports 28, 34 of valve 26 and actuated to flood the chamber 14 with sterile saline. A vacutainer connected to tubing 24 may then be utilized in a manner similar to that disclosed above to draw the saline from the chamber 14, through tubing 24 and into the vacutainer. In the case where a vacutainer is not utilized, sterile air can be injected through the valve 26 to push the saline from the chamber 14 into the purge receptacle via line 24. In yet another embodiment, the valves 20, 26 may be controlled so that a syringe connected to valve 26 is in fluid communication with the chamber 14, and so that chamber 14 is in fluid communication with the sample source 12. The syringe can then be utilized to push fluid inboard of the valve 20 back into the sample source 12 by gravity. In an embodiment, the vertical orientation of the graduated chamber 14 assists in measuring and emptying. It is contemplated that in some embodiments, a check valve may be positioned inboard of the valve 20 for preventing fluid from being inadvertently pushed back into the sample source 12.

In connection with the above, in an embodiment, the second valve 26 may be omitted in favor of a single port. A user can then just unscrew the syringe 18 after using it to draw the fluid from the sample source 12 into the chamber 14 to let air in through the sterile air filter.

Figure 2:
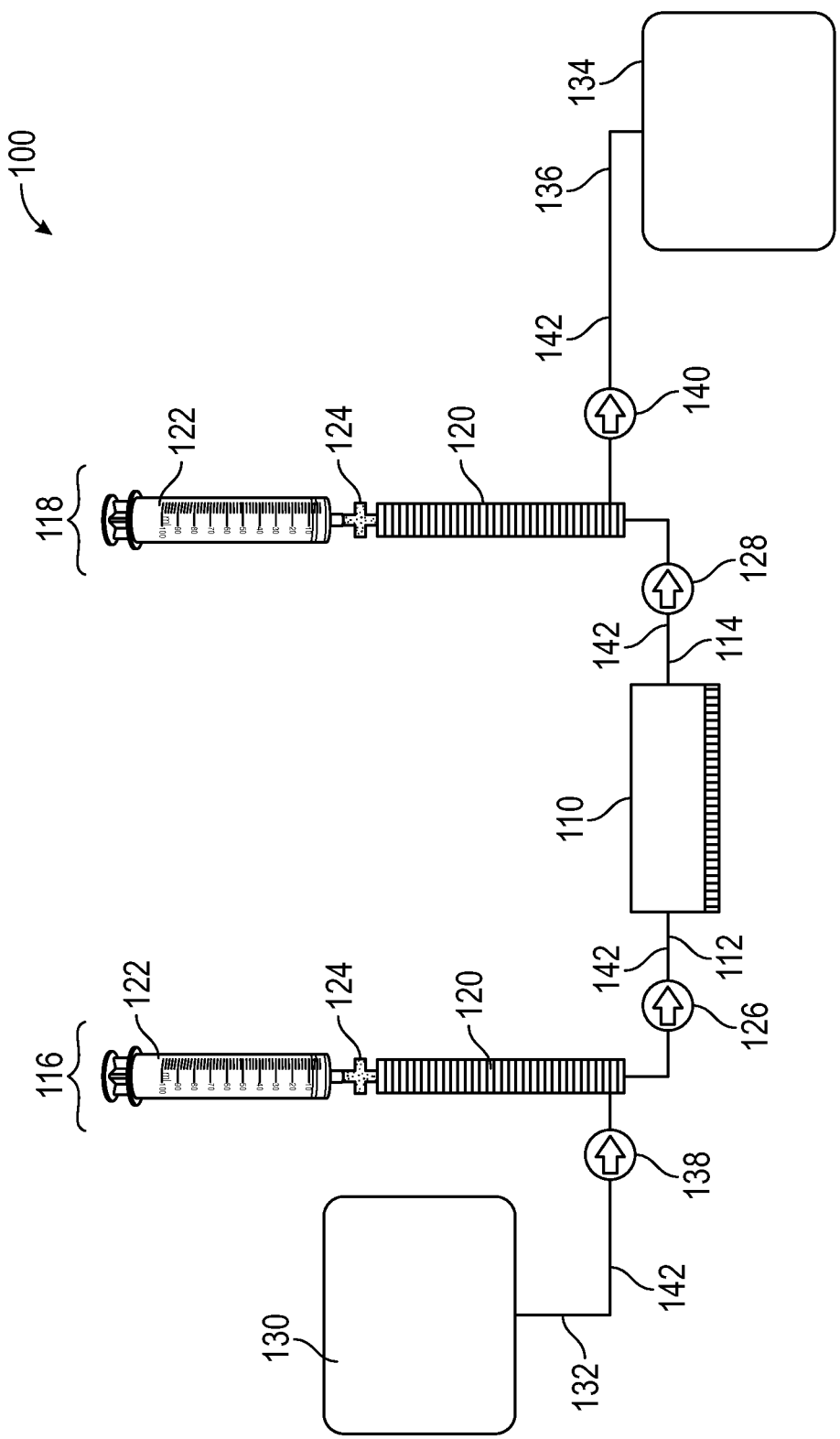
FIG. 2 is a schematic representation of an exemplary bioprocessing assembly, according to another embodiment of the invention.

Referring now to FIG. 2, a bioprocessing assembly 100 (also referred to herein as bioprocessing system 100 or sampling assembly 100) according to another embodiment of the invention is shown. The bioprocessing assembly 100 includes a culture vessel 110 which may be, for example, a static culture vessel containing a population of cells. As illustrated, the vessel 110 includes two tubing tails 112, 114 (e.g., connected to opposing ends of the vessel 110), and two manual syringe pumps 116, 118 welded to the tubing tails 112, 114, respectively. The manual syringe pumps 116, 118 are generally similar in configuration to those described above in connection with FIG. 1. In particular, manual syringe pumps 116, 118 each include a graduated chamber 120 having a plurality of graduations thereon for visually determining a volume of fluid within the chamber 120. Each of the pumps 116, 118 also include a pump device such as a manual syringe 122 configured for fluid connection to an upper end of the chamber 120. A sterile air filer 124 is disposed intermediate the chamber 120 and the syringe 122. In an embodiment, the sterile air filer 124 is permanently attached to the chamber 120. In other embodiments, the sterile air filter 124 may be connected via a luer taper to the syringe 122.

The graduated chambers 120 of the first and second syringe pumps 116, 118 are in fluid communication with the vessel 110 via the tubing tails 112, 114, respectively. In an embodiment, a check valve 126, 128 is positioned along the fluid pathway (i.e., along the tubing tails 112, 114) between the vessel 110 and the chambers of the syringe pumps 116, 118, respectively, permitting only unidirectional flow of fluid as indicated by the arrows.

As further shown in FIG. 2, the bioprocessing assembly 100 may further include a source reservoir 130 fluidly connected to the graduated chamber 120 of the first syringe pump 116 via tubing 132, and a waste reservoir 134 fluidly connected to the graduated chamber 120 of the second syringe pump 118 via tubing 136. As discussed hereinafter, the source reservoir 130 may contain various fluids for use in bioprocessing operations such as, for example, fresh media, coating solution, virus, etc. As illustrated, both tubing runs 132, 136 may be fitted with check valves 138, 140 which permit only unidirectional flow of fluid (e.g., from the fluid source 130 to the chamber 120 of the first syringe pump 116, and from the chamber 120 of the second syringe pump 118 to the waste reservoir 134) as indicated by the arrows. In an embodiment, the various components of the assembly 100 may be fluidly interconnected at sterile weld points 142 along the tubing lengths.

As will be appreciated, the syringe pump 116 (and the syringe 122 thereof) allows for the aseptic transfer of fluid from the source reservoir 130 to the vessel 110 and/or from the vessel 110 to a waste receptacle 134 or other downstream bag or receptacle. In particular, syringe 116 may be utilized in a manner similar to that described above in connection with FIG. 1 to draw a fluid from the source reservoir 130, through the tubing 132, and into the graduated collection chamber 120 of the first syringe pump 116. As disclosed above, the graduations on the chamber 120 allow a user to precisely control the amount of fluid drawn into the chamber. The same or different syringe or pump can then be used to push air through the sterile air filter 124, thereby pushing the fluid within the chamber 120 through tubing 112 and into the vessel 110. In an embodiment, the fluid may be moved from the chamber 120 of the first syringe pump 116 to the vessel 110 under force of gravity. Syringe pump 118 can be operated in similar manner to move fluid from the vessel 110 to the waste receptacle 134, by drawing fluid out of vessel 110 and into the chamber 120 through tubing 114 via actuation of the syringe 122, and then by pushing air into the chamber 120 through sterile air filter 124 to move the fluid from the chamber 120 to waste receptacle 134 through tubing 136. In an embodiment, the fluid may be moved from the chamber 120 of the second syringe pump 118 to the waste receptacle 134 under force of gravity.

The assembly 100 of the invention shown in FIG. 2, therefore, can be utilized to carry out a variety of bioprocessing operations, such as perfusion. Where manual syringe pumps are utilized, it is envisioned that such perfusion would be sporadic, pulse perfusion (carried out at selected intervals). For example, using the assembly 100, manual pulsed perfusion may be carried out at an approximate rate of 0.5 L/day (which would require, for example, 5 100 mL volumes per day). It is contemplated, however, that perfusion can be carried out automatically, and in a continuous or pulsed manner, using a mechanical pump instead of a manual syringe. In particular, while FIG. 2 illustrates the use of a manual syringe, other manual, semi-automatic, or automatic pump devices (e.g., a motorized pump) may also be utilized without departing from the broader aspects of the invention.

As with the embodiment of FIG. 1, the syringes 122 of the pumps 116, 118 serve solely as a means to create a vacuum to draw fluid into the graduated chambers 120 of the pumps 116, 118, respectively, or to create positive pressure to dispel fluid. Accordingly, with this configuration there are no worries of contamination as the syringes 122 are not part of the fluid paths (i.e., they never come into contact with the fluid moving into or out of the source reservoir 130, culture vessel 110 or waste receptacle 134. Accordingly, in any of the embodiments disclosed herein, the syringe pumps and components thereof need not even be sterile, as they never come into contact the bioprocess fluid. In this manner, the assembly 100 provides a fully closed manual culture system that obviates sterility and contamination issues that have not been solved using existing systems and methods.

In addition to the configuration of the assembly 100 shown in FIG. 2, it is further contemplated that the assembly 100 may include pump devices similar to pump devices 116, 118 or that disclosed above in connection with FIG. 1 for aseptically pulling samples or to make small volume additions to the vessel 110. In this way, the assembly 100 can be utilized to draw a sample from the vessel 110 for testing of the fluid (e.g., for determining cell density).

Figure 3:
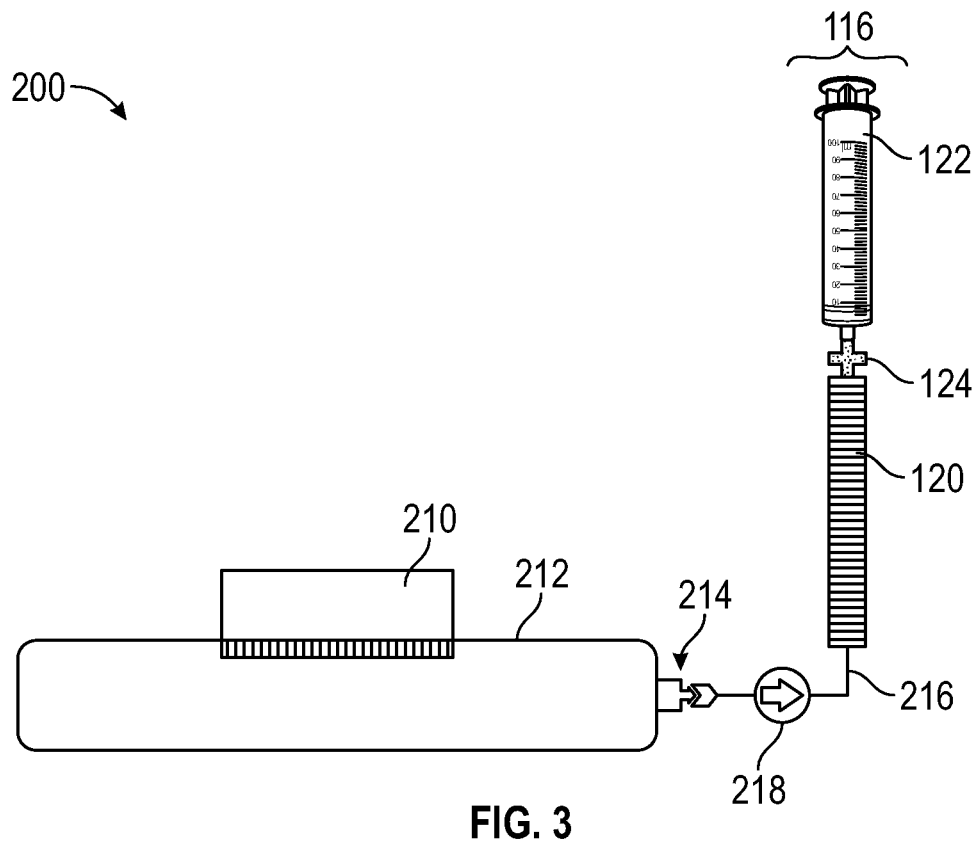
FIG. 3 is a schematic representation of an exemplary sampling assembly for a bioprocessing system according to another embodiment of the invention.

Turning now to FIG. 3, an aseptic sampling assembly 200 in the context of a recirculating loop according to another embodiment of the invention is illustrated. The sampling assembly 200 includes a bioreactor vessel 210 in the form of, for example, a static culture vessel containing a population of cells, and a recirculating loop 212 (e.g., formed from tubing and having a pump (not shown) to circulate the fluid) having a first end fluidly connected to an outlet of the vessel 210 for receiving fluid from the vessel 210, and a second end also fluidly connected to the vessel 210 for returning the fluid to the vessel 210. The sampling assembly 200 further includes a manual syringe pump 116 fluidly connected to the recirculating loop 212. In an embodiment the manual syringe pump 116 is similar or identical to the manual syringe pump 116, 118 of FIG. 2, where like reference numerals designate like parts. A length of tubing 216 having an optional check valve 218 serves to connect the chamber 120 to the recirculating loop 212. In an embodiment, the syringe pump 116 is fluidly connected to the recirculating loop 212 via a sterile connector 214. The sterile connector 214 may be, for example, a reusable sterile connector. In an embodiment, the reusable half of the sterile connector 214 may be part of the kit (containing the vessel 210 and recirculating loop), while a single-use mating portion may be part of a sampling accessory (comprising the manual syringe pump 116 including chamber 120, tubing 216 and check valve 218).

In use, cells reside in the vessel 210, but for a sampling event, are recirculated through the loop 212 to ensure homogeneity. A sample can then be manually pulled from the recirculating fluid using syringe pump 116 in the manner hereinbefore described. As indicated above, the manual syringe pump 116 connects aseptically to the loop 212 via the reusable aseptic or sterile connector 214. To collect a sample, a user would first connect the syringe pump 116 to the recirculating loop 212 via the connector 214. Then, through manual action of the syringe 122, a sample is pulled through the tubing 216, past the check valve 218, and into the graduated chamber 120. As disclosed above, the chamber 120 is graduated so as to allow a user to see the precise volume being pulled, and provides a means to pull a sample of any desired volume. As also indicated above, the syringe 122 is attached to the chamber 120 via an intermediate sterile air filter 124 to mitigate the risk of accidentally back-flushing non-sterile air into the system. This risk can be further mitigated by inclusion of check valve 218 along tubing line 216. Omitting the check valve 218, however, allows for aseptic backflushing into the loop 212 in the manner described above in connection with FIG. 1.

While FIG. 3 illustrates the use of a manual syringe, other manual, semi-automatic, or automatic pump devices (e.g., a motorized pump) may also be utilized to carry out the sampling operations disclosed herein, without departing from the broader aspects of the invention. Moreover, while the system 200 of FIG. 3 discloses the use of a reusable connector 214, it is contemplated that multiple ports along the recirculation loop 212 may, alternatively, be employed for the withdrawal of multiple samples.

Figure 4:
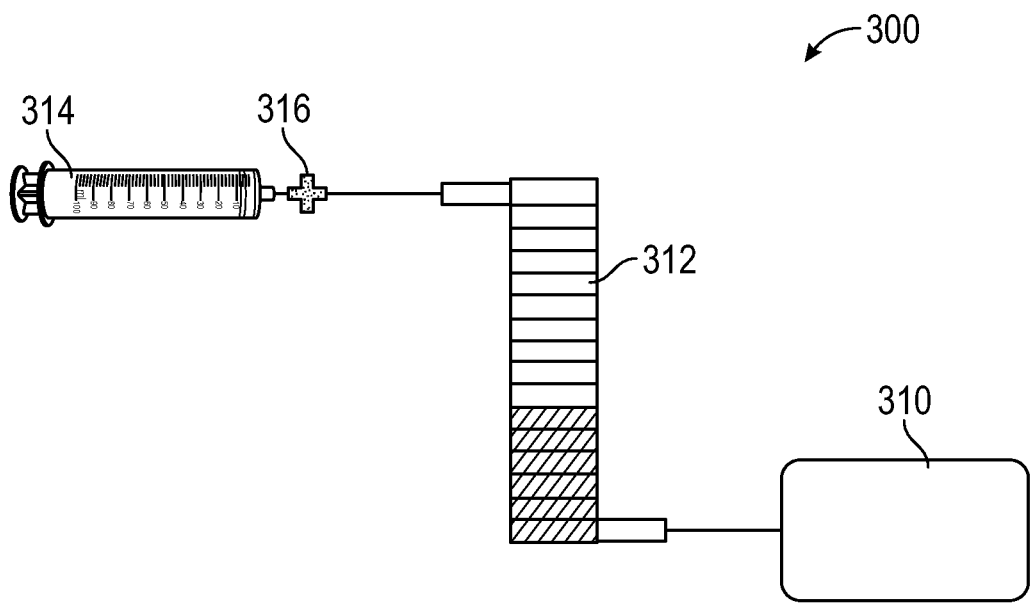
FIG. 4 is a schematic representation of an exemplary sampling assembly according to an embodiment of the invention, illustrating a sampling operation.
Figure 5:
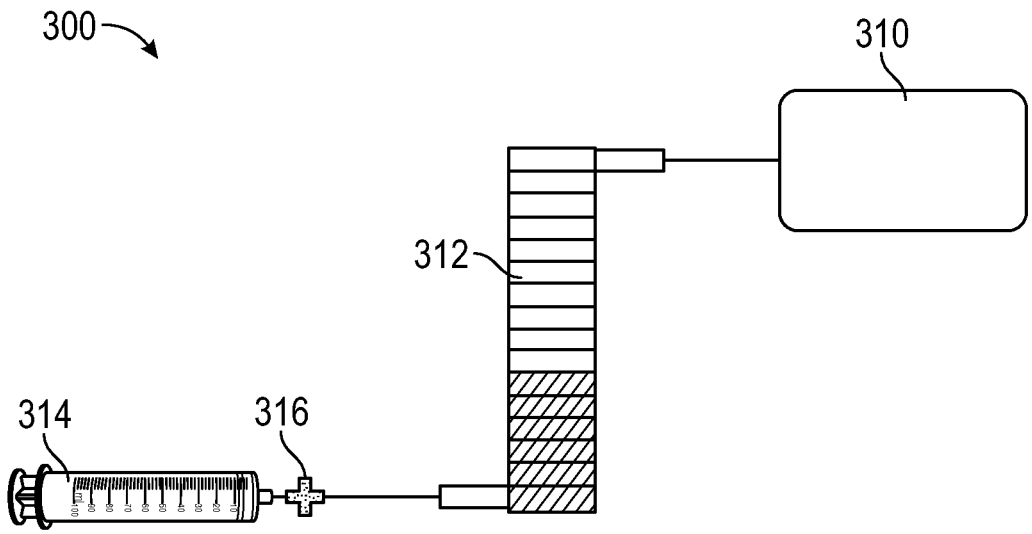
FIG. 5 is a schematic representation of the sampling assembly of FIG. 4, illustrating a flushing operation.

With reference to FIGS. 4 and 5, a sampling assembly 300 for use in a bioprocessing system according to an embodiment of the invention is shown. The sampling assembly 300 is similar to the syringe pump disclosed above in connection with FIGS. 1-3, and includes a bioprocessing vessel such as, for example, a single use bioreactor 310 containing a fluid (e.g., a cell culture). The sampling assembly 300 includes a graduated chamber 312 fluidly connected to the single use bioreactor 310, and a syringe 314 fluidly connected to the graduated chamber 312. A sterile air filter 316 is disposed between the syringe 314 and the graduated chamber 312 for the purpose hereinbefore described. The sampling assembly 300 is operable in the manner described above in connection with FIG. 1, to draw a sample from the single use bioreactor 310 into the graduated chamber 312.

As illustrated in FIGS. 4 and 5, in an embodiment, the single use bioreactor is fluidly connected to the chamber 312 at one end of the chamber 312 (i.e. top or bottom), while the syringe 314 is fluidly connected to the chamber 312 at an opposite end of the chamber 312 (i.e., bottom or top). With particular reference to FIG. 4, to pull a sample, the chamber is oriented such that fluid is drawn from the bioreactor vessel 310 into the bottom of the chamber 310 (while the syringe 314 draws air out of the chamber 310 from the top). This process is carried out until a desired amount of fluid is present in the chamber 310, as visually indicated to a user by the markings on the chamber 310. With particular reference to FIG. 5, to purge or flush the chamber 310 and flow lines (such as the process contemplated in the discussed of FIG. 1), in an embodiment, the sampling assembly 300 is inverted such that the syringe and connection to the chamber 310 is located vertically below the connection point of the bioreactor vessel 310 to the chamber. The syringe 314 is then depressed. Air will bubble up through the fluid within the graduated chamber 310 and back down the flow lines/tubing to the bioreactor vessel 310, thereby purging the lines.

Figure 6:
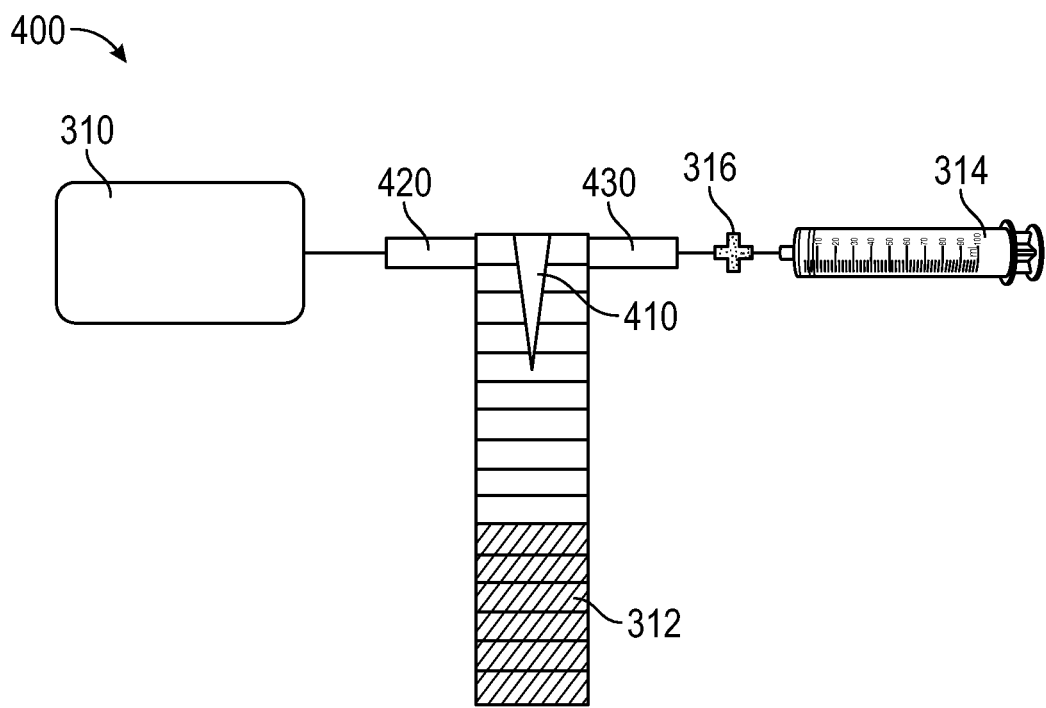
FIG. 6 is a schematic representation of an exemplary sampling assembly according to another embodiment of the invention.

Turning now to FIG. 6, a sampling assembly 400 according to another embodiment of the invention is shown. The sampling assembly 400 is similar to sampling assembly 300 of FIGS. 4 and 5, where like reference numerals designate like parts. Rather than having the syringe 314 and bioreactor vessel 310 connect to the graduated chamber 312 at opposite ends thereof, however, the syringe 314 and bioreactor vessel 310 are both fluidly connected to an upper end portion of the graduated chamber 312 (on opposing sides of the chamber 312). In such embodiment, the graduated chamber 312 includes a baffle 410 or divider that extends downwardly into the interior area of the chamber 312 from the top thereof.

In use, to pull a sample from the bioreactor vessel 310, the syringe 314 is used in the manner disclosed above to pull fluid into the graduated chamber 312. Fluid will fill the chamber 312, through port 420, entering from the top port connection to the bioreactor vessel 310 and collecting at the bottom therefore due to the force of gravity. The baffle 410 serves to prevent pulling fluid straight across to the syringe 314. To purge or flush the flow lines, the syringe 314 is depressed to push air through the sterile air filter 316 and port 430 and into the graduated chamber 312. The air will circuit around the baffle 410, through the fluid (in the case that the fluid extends to the baffle), and back down the line to the bioreactor vessel 310.

Figure 8:
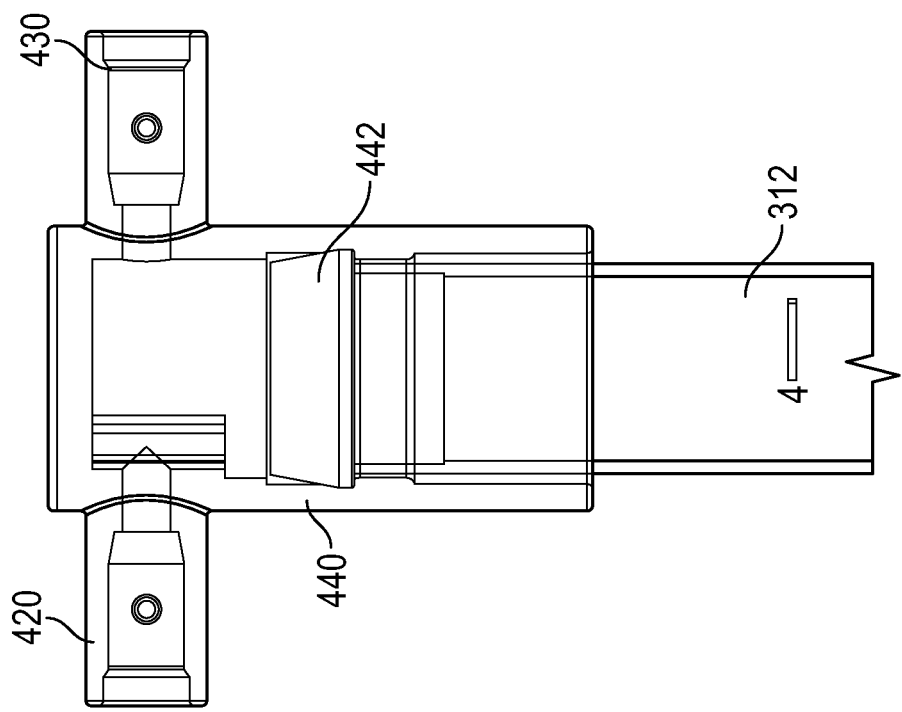
FIG. 8 is another enlarged, detail view of a portion of a graduated sampling chamber of the assembly of FIG. 6.
Figure 7:
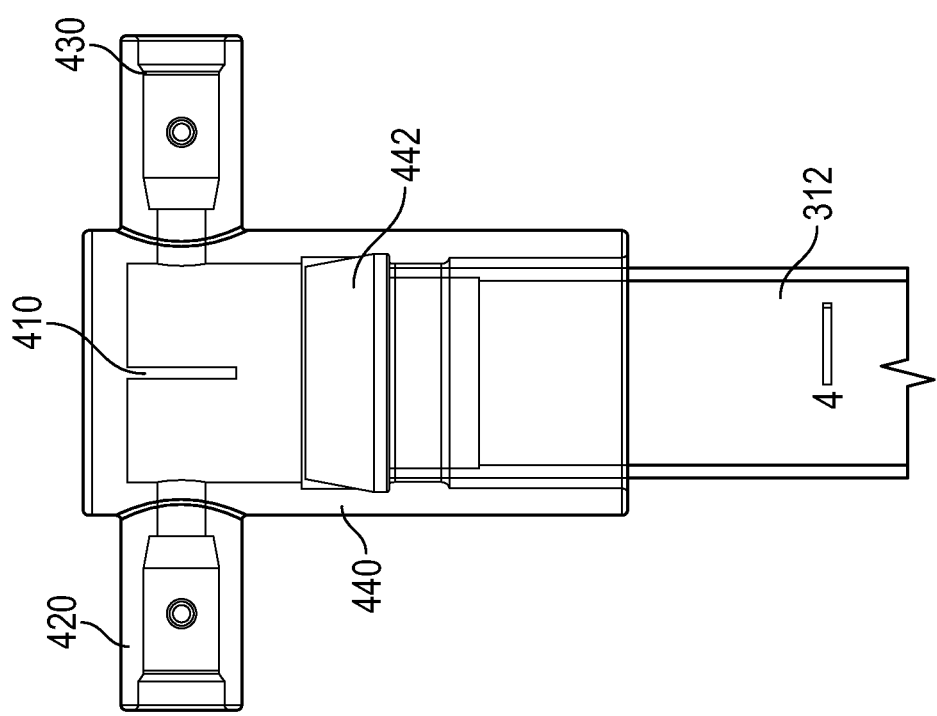
FIG. 7 is an enlarged, detail view of a portion of a graduated sampling chamber of the assembly of FIG. 6.

With reference to FIGS. 7 and 8, in an embodiment, the port connections 420, 430 to the bioreactor vessel 310 and syringe 314, respectively, may be integrated into a cap 440 of the graduated chamber 312, which is configured to be received at the top the graduated chamber 312. In this respect, and as shown in FIGS. 7 and 8, the graduated chamber 312 includes a rubber stopper 442 fitted in the neck of the chamber 312 that is designed to frictionally engage the cap 440 for removable coupling of the cap 440 to the chamber 312. While a friction fit is illustrated in FIGS. 7 and 8, it is contemplated that other means of releasable connection such as threaded engagement, a bayonet mount, and the like may also be utilized without departing from the broader aspects of the invention. As will be appreciated, this configuration allows the cap 440 to be removed so as to access the collected sample (rather than having to push it to a separate collection receptacle as disclosed in FIG. 1.

Figure 9:
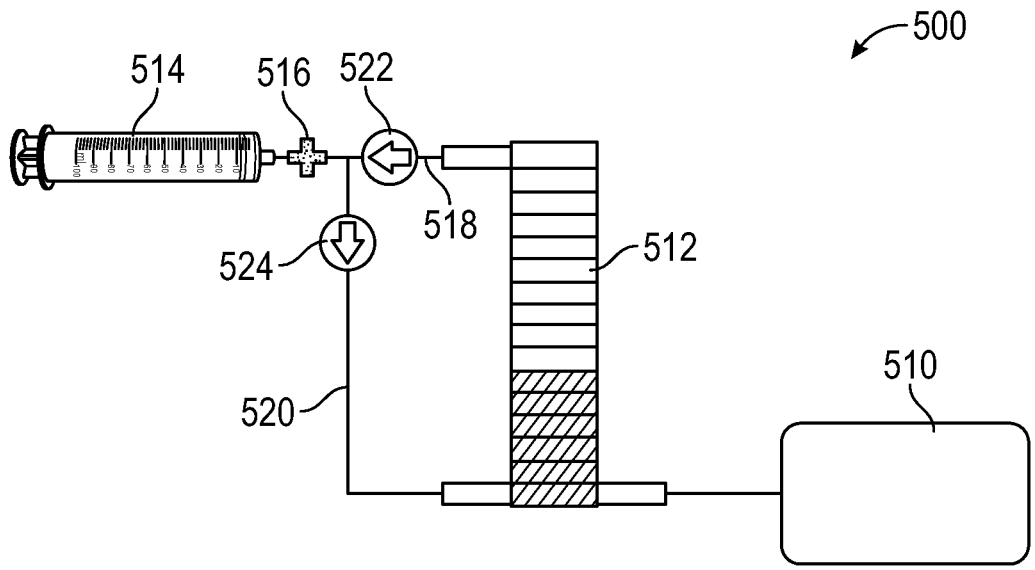
FIG. 9 is a schematic representation of an exemplary sampling assembly according to an embodiment of the invention, illustrating a sampling operation.
Figure 10:
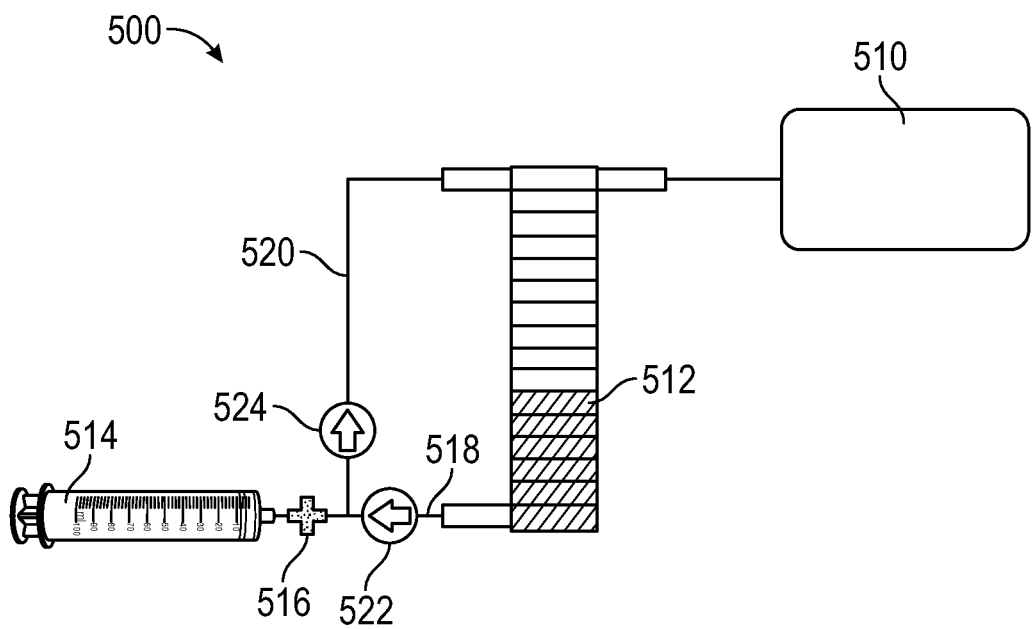
FIG. 10 is a schematic representation of the sampling assembly of FIG. 4, illustrating a flushing operation.

Referring now to FIGS. 9 and 10, a sampling assembly 500 for use in a bioprocessing system according to an embodiment of the invention is shown. The sampling assembly 500 is similar to those described above, and includes a bioprocessing vessel such as, for example, a single use bioreactor 510 containing a fluid (e.g., a cell culture). The sampling assembly 500 includes a graduated chamber 512 fluidly connected to the single use bioreactor 510, and a syringe 514 fluidly connected to the graduated chamber 512. A sterile air filter 516 is disposed between the syringe 514 and the graduated chamber 512 for the purpose hereinbefore described. As shown in FIG. 9, the bioreactor vessel 510 is fluidly connected to the graduated chamber 512 at one end thereof, while the syringe 514 is fluidly connected to the same end of the graduated chamber 512 via a first tubing line 518 and to an opposite end of the graduated chamber via a second tubing line 520. As illustrated, the first tubing line 518 includes a check valve 522 that only permits flow out of the bioreactor vessel 510, while the second tubing line 520 includes a check valve 524 that only permits flow into the bioreactor vessel 510.

With particular reference to FIG. 9, in use, to obtain a sample from the bioreactor vessel 510, a user uses the syringe 514 to pull fluid into sampling chamber 512 in the manner hereinbefore described. Fluid will fill the chamber from the bottom, as shown in FIG. 9. With reference to FIG. 10, to flush or purge the lines, the sampling assembly 500 is inverted similar to the manner described above in connection with FIGS. 4 and 5. The syringe 514 is then depressed to force air into the chamber 512 through the sterile air filter 516 and through the second tubing line 520. The check valves 522, 524 will force the air down the external bypass path (i.e., through line 520), over the fluid and sweep the line back into the bioreactor vessel 510.

It is contemplated that any of the embodiments of FIGS. 4-10 may be integrated into the assemblies/systems of FIGS. 1-3. Moreover, similar to FIGS. 1-3, while the embodiments of FIGS. 4-10 illustrate the use of the use of a syringe, other manual, semi-automatic, or automatic pump devices (e.g., a motorized pump) may also be utilized to carry out the sampling and purging operations disclosed herein, without departing from the broader aspects of the invention.

As discussed above, embodiments of the invention relate to pump devices and related methods to add or remove a known volume of fluid to or from a fluidic vessel in a functionally closed manner. The embodiments of the invention described herein are very simple and may be deployed as completely manual or as semi- or fully automated. In addition, the embodiments of the invention disclosed herein provide the ability to collect samples or make additions of almost any volume, in a repeatable and precise manner.

While the embodiments of the invention relate generally to pump devices and related methods to add or remove a known volume of fluid to or from a fluidic vessel in a functionally closed manner, the invention is not so limited in this regard, and it is contemplated that the inventive concepts disclosed herein may be applied to certain existing systems and devices to improve the functionality thereof. For example, the main chamber in the Sefia and Sepax devices from Cytiva is essentially a syringe barrel (that also capable of centrifugation), which can be utilized as the syringe in the embodiments of the invention disclosed herein. Moreover, for repeated sampling of a cell culture chamber, a variation of the inventive device (of suitable volume capacity) could be used either in true single-use fashion (a fresh device for every sample, for maximum reduction of contamination risk) or repeatedly for the duration of culture. The latter scenario would require the ability to flush the line of residue after each sampling event, such as by using the process disclosed above in connection with FIG. 1.

In an embodiment, a sampling system is provided. The sampling system includes a graduated sampling chamber configured for fluid connection to a sample source, a pump device configured for fluid connection with the sampling chamber, and a sterile air filter intermediate the pump device and the sampling chamber, wherein the pump device is selectively actuatable to draw a volume of fluid from the sample source into the sampling chamber. In an embodiment, the sampling chamber includes a baffle separating an inlet, where the fluid enters the sampling chamber, from an outlet, where the pump draws air from the sampling chamber. In an embodiment, the system includes a first valve intermediate the sampling chamber and the sample source, the first valve permitting unidirectional flow of the fluid from the sample source to the sampling chamber. In an embodiment, the sampling chamber is configured for fluid connection to the sample source at a location adjacent to a bottom of the sampling chamber, the sampling chamber is configured for fluid connection to the pump device at a location adjacent to a top of the sampling chamber. In an embodiment, the system also includes a first valve intermediate the sampling chamber and the sample source, and a sample collection line fluidly connected to the sampling chamber via the first valve, wherein the first valve is actuatable to selectively place the sample source and/or the sample collection line in fluid communication with the sampling chamber. In an embodiment, the first value is movable to a first position where the sampling chamber is in fluid communication with the sample source, such that the pump device is operable draw the volume of fluid into the sampling chamber, and the first valve is movable to a second position where the sampling chamber is in fluid communication with the sample line so that the volume of fluid in the sampling chamber can flow from the sampling chamber through the sample collection line. In an embodiment, the pump device is a syringe. In an embodiment, the pump device is an automated pump. In an embodiment, the system includes a receptacle in fluid communication with the sample collection line. In an embodiment, the receptacle is a vacutainer. In an embodiment, the sample source is one of a cell culture vessel or a circulation loop. In an embodiment, the system further includes a second chamber configured for fluid connection to a media source via an inlet port and for fluid connection to the cell culture vessel or the circulation loop via an outlet port, a second pump device configured for fluid connection with the second chamber, a first valve intermediate the second chamber and the media source, the first valve permitting unidirectional flow from the media source to the second chamber, and a second valve intermediate the second chamber and the cell culture vessel or the circulation loop, the second valve permitting unidirectional flow from the second chamber to the cell culture vessel or the circulation loop. The second pump device is selectively actuatable to draw a volume of fluid from the media source into the second chamber, and to push the volume of fluid from the second chamber into the cell culture vessel or the circulation loop.

In another embodiment of the invention, a method for sampling is provided. The method includes the steps of connecting a sampling chamber to a sample source, and actuating a pump to draw a volume of fluid from the sample source through a valve, and into the sampling chamber, wherein the valve is configured to prevent backflow of fluid from the sampling chamber to the sample source. In an embodiment, the valve is one of a check valve or a stopcock. In an embodiment, the step of actuating the pump to draw the volume of fluid into the sampling chamber includes evacuating air from the sampling chamber through an outlet, wherein the outlet is configured with a sterile air filter. In an embodiment, the pump is a syringe, and the sampling chamber has graduated markings. In an embodiment, the method may also include the steps of opening a second valve to place a sampling line in fluid communication with the sampling chamber, and flowing the volume of fluid from the sampling chamber to the sampling line. In an embodiment, the step of flowing the volume of fluid from the sampling chamber to the sampling line includes pushing air into the sampling chamber through a sterile air filter to displace the volume of fluid from the sampling chamber.

In yet another embodiment, a bioprocessing system is provided. The bioprocessing system includes a cell culture vessel, and a first assembly for adding a first fluid to the cell culture vessel. The first assembly includes a first chamber configured for fluid connection to a source of the first fluid via an inlet port in the first chamber, and for fluid connection to the cell culture vessel via an outlet port in the first chamber, a first pump device configured for fluid connection with the first chamber, a first valve intermediate the first chamber and the source, the first valve permitting unidirectional flow from the source to the first chamber, and a second valve intermediate the first chamber and the cell culture vessel, the second valve permitting unidirectional flow from the first chamber to the cell culture vessel. The second pump device is selectively actuatable to draw a volume of the first fluid from the source into the first chamber, and to push the volume of fluid from the first chamber into the cell culture vessel. The bioprocessing system also includes second assembly for removing a second fluid from the cell culture vessel. The second assembly includes a second chamber configured for fluid connection to the cell culture vessel via an inlet port in the second chamber, and for fluid connection to a collection vessel via an outlet port in the second chamber, a second pump device configured for fluid connection with the second chamber, a third valve intermediate the cell culture vessel and the second chamber, the third valve permitting unidirectional flow from the cell culture vessel to the second chamber, and a fourth valve intermediate the second chamber and the collection vessel, the fourth valve permitting unidirectional flow from the second chamber to the collection vessel. The second pump device is selectively actuatable to draw a volume of the second fluid from the cell culture vessel into the second chamber, and to push the volume of fluid from the second chamber into the collection vessel. In an embodiment, the first pump and the second pump are syringes, and the first chamber and the second chamber have graduated markings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sampling system, comprising:
a sample source having a volume of fluid;
a first graduated sampling chamber;
a first flow line fluidly connecting the sample source with the first graduated sampling chamber;
a first check valve operatively coupled to the first flow line intermediate of the first graduated sampling chamber and the sample source, the first check valve having a direct connection with the first graduated sampling chamber via the first flow line without any additional components therebetween, wherein the first check valve is configured to permit only unidirectional flow of the fluid from the sample source to the first sampling chamber via the first flow line, and wherein the flow of the fluid from the sample source to the first graduated sampling chamber flows directly from the first check valve into the first graduated sampling chamber without passage through any additional components operatively coupled to the first flow line between the sample source and the first graduated sampling chamber;
a first pump device configured for fluid connection with the first graduated sampling chamber;
a sterile air filter intermediate the first pump device and the first graduated sampling chamber;
a media source;
a second graduated sampling chamber configured for fluid connection to the media source via an inlet port and for fluid connection to the sample source via an outlet port; and
a second pump device configured for fluid connection with the second graduated sampling chamber;
wherein the first pump device is selectively actuatable to draw the volume of fluid from the sample source into the first graduated sampling chamber without the volume of fluid contacting the first pump device,
wherein the second pump device is selectively actuatable to draw a volume of fluid from the media source into the second graduated sampling chamber, and to push the volume of fluid from the second graduated sampling chamber into the sample source.

2. The sampling system of claim 1, wherein:
the first graduated sampling chamber includes a baffle separating an inlet, where the fluid enters the first graduated sampling chamber, from an outlet, where the first pump draws air from the first graduated sampling chamber.

3. The sampling system of claim 1, wherein:
the first graduated sampling chamber is configured for fluid connection to the sample source at a location adjacent to a bottom of the first graduated sampling chamber; and
the first graduated sampling chamber is configured for fluid connection to the first pump device at a location adjacent to a top of the first graduated sampling chamber.

4. The sampling system of claim 1, wherein:
the first pump device is a syringe.

5. The sampling system of claim 1, wherein:
the first pump device is an automated pump.

6. The sampling system of claim 1, further comprising:
a sample collection line fluidly connected to the first graduated sampling chamber; and
a receptacle in fluid communication with the sample collection line.

7. The sampling system of claim 6, wherein:
the receptacle is a vacutainer.

8. The sampling system of claim 1, wherein:
the sample source is one of a cell culture vessel or a circulation loop.

9. The sampling system of claim 8, further comprising:
a second check valve intermediate the second graduated sampling chamber and the media source, wherein the second check valve is configured to permit only unidirectional flow from the media source to the second graduated sampling chamber;
a third check valve intermediate the second graduated sampling chamber and the cell culture vessel or the circulation loop, wherein the third check valve is configured to permit only unidirectional flow from the second graduated sampling chamber to the cell culture vessel or the circulation loop.

\* \* \* \* \*